US010953431B2

(12) United States Patent
Josten et al.

(10) Patent No.: US 10,953,431 B2
(45) Date of Patent: Mar. 23, 2021

(54) COATING METHOD AND WORKPIECE

(71) Applicant: Gerresheimer Bünde GmbH, Bünde (DE)

(72) Inventors: Stefan Josten, Bielefeld (DE); Frank Wittland, Enger (DE); Stephan Brückner, Mackenrode (DE); Christoph Gerhard, Friedland (DE); Wolfgang Viöl, Adelebsen (DE)

(73) Assignee: GERRESHEIMER BÜNDE GMBH, Bünde (DE)

( * ) Notice: Subject to any disclaimer, the term of this patent is extended or adjusted under 35 U.S.C. 154(b) by 199 days.

(21) Appl. No.: 16/040,686

(22) Filed: Jul. 20, 2018

(65) Prior Publication Data

US 2019/0030564 A1 Jan. 31, 2019

(30) Foreign Application Priority Data

Jul. 27, 2017 (DE) ...................... 10 2017 212 974.3

(51) Int. Cl.
| | | |
|---|---|---|
| *B05D 3/14* | (2006.01) | |
| *C09J 5/02* | (2006.01) | |
| *B05D 3/02* | (2006.01) | |
| *A61M 5/34* | (2006.01) | |
| *B29C 65/48* | (2006.01) | |
| *B29C 65/00* | (2006.01) | |
| *B29L 31/00* | (2006.01) | |

(52) U.S. Cl.
CPC ............ *B05D 3/148* (2013.01); *A61M 5/349* (2013.01); *B05D 3/0254* (2013.01); *B05D 3/145* (2013.01); *B29C 65/48* (2013.01); *B29C 66/612* (2013.01); *C09J 5/02* (2013.01); *A61M 2207/00* (2013.01); *B29L 2031/7544* (2013.01); *C09J 2433/00* (2013.01); *C09J 2463/00* (2013.01); *C09J 2475/00* (2013.01)

(58) Field of Classification Search
None
See application file for complete search history.

(56) References Cited

U.S. PATENT DOCUMENTS

| | | | | |
|---|---|---|---|---|
| 4,524,089 | A | 6/1985 | Haque et al. | |
| 4,894,254 | A * | 1/1990 | Nakayama ............. | B05D 3/145 427/539 |
| 6,331,174 | B1 | 12/2001 | Reinhard et al. | |
| 2006/0157453 | A1 | 7/2006 | Dumont et al. | |
| 2009/0010985 | A1* | 1/2009 | Sakhrani ............... | C10M 107/50 424/422 |
| 2010/0285319 | A1* | 11/2010 | Kwak ...................... | C08J 7/123 428/411.1 |
| 2010/0304156 | A1 | 12/2010 | Sato et al. | |
| 2012/0248065 | A1* | 10/2012 | Kawamura ............ | B82Y 10/00 216/66 |
| 2012/0321776 | A1* | 12/2012 | Vetrecin ................. | B05D 3/147 427/2.1 |
| 2014/0116335 | A1* | 5/2014 | Tsuji ...................... | C23C 16/482 118/620 |
| 2015/0165125 | A1* | 6/2015 | Foucher .............. | A61M 5/3129 604/230 |

FOREIGN PATENT DOCUMENTS

| | | |
|---|---|---|
| DE | 10 2008 009 171 A1 | 8/2009 |
| EP | 0201915 B1 | 1/1990 |
| EP | 0 709 105 A1 | 5/1996 |
| EP | 1 352 667 B1 | 12/2004 |
| FR | 2 840 826 | 12/2003 |
| JP | H0341176 A | 2/1991 |
| WO | WO 99/57185 | 11/1999 |
| WO | WO 2016/124824 A1 | 8/2016 |

OTHER PUBLICATIONS

English translation of G. Scholz et al., "Verklebung von wachsimprägnierter Buche unter Variation der Klebesysteme und Durchführung einer Plasmabehandlung," ("Adhesion of wax impregnated solid beech wood with different glues and by plasma treatment") European Journal of Wood and Wood Products, dated Apr. 28, 2010, pp. 315-321, vol. 68, Issue 3, DOI 10.1007/s00107-010-0466-2, published online by Springer-Verlag, Berlin, Germany.

Liqing Yang et al., "Surface modification of a biomedical polyethylene terephthalate (PET) by air plasma," Applied Surface Science, dated Nov. 27, 2008, pp. 4446-4451, vol. 255, Issue 8, published by Elsevier B.V., Amsterdam, Netherlands.

(Abstract in English) G. Scholz et al., "Verklebung von wachsimprägnierter Buche unter Variation der Klebesysteme and Durchführung einer Plasmabehandlung," European Journal of Wood and Wood Products, dated Apr. 28, 2010, pp. 315-321, vol. 68, Issue 3, DOI 10.1007/s00107-010-0466-2, published online by Springer-Verlag, Berlin, Germany.

Vera-Maria Graubner et al., "Incubation and ablation behavior of poly(dimethylsiloxane) for 266 nm irradiation," Applied Surface Science, dated 2002, pp. 786-790, vols. 197-198, published by Elsevier Science B.V., Amsterdam, Netherlands.

András Tóth et al., "Oxidative Damage and Recovery of Silicone Rubber Surfaces. I. X-ray Photoelectron Spectroscopic Study," Journal of Applied Polymer Science, dated Nov. 30, 1993, pp. 1293-1307, vol. 52, published by John Wiley & Sons, Inc., Hoboken, New Jersey.

(Continued)

*Primary Examiner* — Marc S Zimmer
(74) *Attorney, Agent, or Firm* — Brinks Gilson & Lione

(57) ABSTRACT

A coating method is provided, in which at least one emulsion and/or one solution is applied at least to a first partial area of a surface of a component, said emulsion and/or solution containing at least one layer-forming substance, and then the component is heat-treated, wherein at least one second partial area of the first partial area is subsequently exposed to a plasma, wherein the carbon content of the coating decreases to less than about 80% or less than about 75% or less than about 70% or less than about 60% of the initial value prior to the plasma treatment. A workpiece and a method for the production thereof is provided.

18 Claims, 4 Drawing Sheets

(56) References Cited

OTHER PUBLICATIONS

S. Dahle et al., "DBD Plasma Treatment of Titanium in O2, N2 and Air," Plasma Chem Plasma Process, dated Jul. 1, 2012, pp. 1-7, published by Springer Science+Business Media, LLC.
A. Helmke et al., "The Acidification of Lipid Film Surfaces by Non-Thermal DBD at Atmospheric Pressure in Air," New Journal of Physics 11, dated Nov. 26, 2009, pp. 1-10, published online at http://www.njp.org/ by IOP Publishing Ltd and Deutsche Physikalische Gesellschaft.
T. C. Manley, "The Electric Characteristics of the Ozonator Discharge," Journal of the Electrochemical Society, dated Oct. 14, 1943, pp. 83-96, vol. 84, Issue No. 1, published online by the Electrochemical Society.
John F. Moulder et al., Handbook of X-ray Photoelectron Spectroscopy, dated Oct. 1992, pp. 1-261, published by Perkin-Elmer Corporation, Physical Electronics Division, Eden Prairie, Minnesota.
"Dow Corning 360—Medical Fluid," Product Information: Healthcare, dated Apr. 6, 2009, pp. 1-5, Dow Corning Corporation, Midland, MI.
"Dow Corning 365—35% Dimethicone NF Emulsion," Product Information: Healthcare, dated May 8, 2004, pp. 1-2, Dow Corning Corporation, Midland, MI.
"Loctite Technical Data Sheet," Loctite 3345, dated Nov. 2004, pp. 1-3, Henkel Technologies, Düsseldorf, Germany.

\* cited by examiner

COATING METHOD AND WORKPIECE

CROSS-REFERENCE TO RELATED APPLICATIONS

This application claims priority under 35 USC § 119 to German Patent Application No. 10 2017 212 974.3, filed Jul. 27, 2017, which is hereby incorporated by reference.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

DETAILED DESCRIPTION

Figure 1:
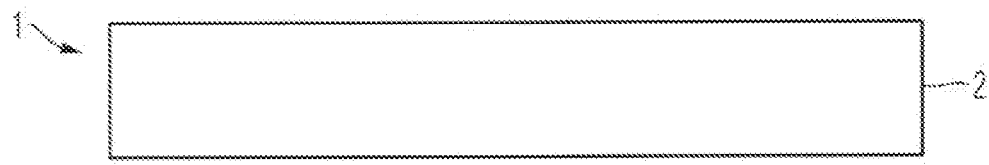
FIG. 1 shows a component intended for coating.

The invention relates to a coating method, in which at least one emulsion and/or one solution is applied at least to a first partial area of a surface of a component, said emulsion and/or solution containing at least one layer-forming substance, and then the component is heat-treated. The invention also relates to a method, in which at least one such component is joined with at least one further component. Finally, the invention relates to a workpiece obtained in this way.

A method of this generic type is known from e.g. EP 1 352 667 A1. This document describes a method for producing an injection syringe, in which the interior of the syringe body is provided with a lubricant at high temperature. The lubricant is subsequently removed again at the joint between syringe body and cannula in order to allow a reliable adhesion of the adhesive used for joining.

This known method has the drawback that the complete removal of the lubricant in a spatially tightly limited area can only be achieved with great effort. Proceeding from this known method, the object of the invention is thus to prepare at least one partial area of a coating in a simple way for a subsequent adhesive bond or also a further coating method.

The invention proposes a coating method, in which at least one emulsion and/or one solution is applied at least to a partial area of a surface of a component, said emulsion and/or solution containing at least one layer-forming substance. In some embodiments of the invention, the component can be made from glass, a plastic material, a metal or an alloy. The component can have a flat or a curved surface. In particular, the component can be a hollow form, the inner surface of which is provided with a coating. In some embodiments of the invention, the component can be a semi-finished product which is further processed in subsequent method steps to give a finished product. In other embodiments of the invention, the component can also be a finished product which, after carrying out the proposed coating method, does not require any further processing.

The coating contains at least one layer-forming substance which is available in the form of an emulsion and/or a solution. The emulsion or the solution contains, in addition to the layer-forming substance, at least one solvent. For the purposes of the present description, the carrier matrix of an emulsion is also referred to as a 'solvent' although the layer-forming substances are only emulsified and not dissolved in the stricter sense.

The emulsion or the solution can be applied to at least one first partial area of the component by methods known per se. In some embodiments of the invention, a full coating of the component can also be provided, i.e. the entire surface of the component is coated according to the invention. The emulsion or the solution can be applied e.g. by spraying, printing, painting or immersion. In order to allow a more uniform coating with the emulsion and/or the solution, additional steps can be taken, e.g. the reduction in the viscosity by heating and/or dilution or a support of the coating by an electric field similar to electrocoating.

According to the invention, the component is heat-treated after the application of the emulsion and/or the solution. The heat treatment can be carried out directly after the application of the emulsion and/or the solution. In other embodiments of the invention, the heat treatment can be carried out after a preceding drying step. On the one hand, the result of the heat treatment is that the solvent of the emulsion and/or the solution is evaporated or driven from the layer. In addition, a bond between the layer-forming substances and the surface of the component can be produced, e.g. by covalent bonds or van der Waals bonds. In some embodiments of the invention, the layer-forming substances can also be cross-linked with one another and e.g. produce a polymer or a polymer-like compound.

In some embodiments of the invention, the coating produced in this way is hydrophobic and/or has improved sliding properties in relation to the untreated surface. In some embodiments of the invention, the produced coating can also be chemically inert with respect to gases or liquids with which the component comes into contact for an intended use.

In a subsequent method step, at least one second partial area of the first partial area of the component that is provided with the coating is subjected to plasma treatment to thus at least partially deactivate or undo the effects of the coating without fully removing the coating per se. A plasma within the meaning of the present description is understood to mean a partially ionized gas which at a predeterminable pressure and with predeterminable composition acts upon at least one second partial area of the coating for a certain period of time. In some embodiments of the invention, the second partial area can be as large as the coated first partial area, such that the plasma acts upon the entire, previously applied coating. If the first partial area comprises the entire surface of the component, the plasma can also act upon the entire surface of the component. In other embodiments of the invention, only part of the coating is subjected to the plasma treatment, whereas other parts of the coating are not exposed to the plasma. For example, partial areas can be subjected to the plasma treatment and are to form a joint in a further method step to thus improve the bond of adhesives or solder or allow it to occur in the first place.

Due to the influence of the plasma, the carbon content of the coating can be reduced to less than about 80% or less than about 75% or less than about 70% or less than about 60% of the initial value prior to the plasma treatment. The reduction in the carbon content can also have the effect that the bonds change within the coating. For example, the coating can be converted from a polymeric structure into a glass-like or amorphous structure.

Finally, the layer thickness in the treated second partial area can be reduced as a result of the action of the plasma. In some embodiments of the invention, the layer thickness can be reduced by more than about 20% or more than about 25% or more than about 30%.

According to the invention, it has, however, been found that the coating is not fully removed by the influence of the plasma. Moreover, a layer thickness of more than about 70% or more than about 60% or more than about 50% of the layer thickness applied in the first method step can be left in the second partial area after the plasma treatment.

In summary, it should be noted that the bonding conditions and/or the layer thickness and/or the inventory of elements of the originally applied coating are changed in the partial area exposed to the plasma as a result of the plasma treatment. This can roughen the coating and/or lead to a hydrophilization so as to facilitate a subsequent coating or joining method or bring it about in the first place. At the same time, the plasma treatment can be carried out more easily than a full removal of the coating which under certain circumstances very strongly adheres to the surface of the component and can only be removed mechanically or wet chemically, wherein, on the one hand, the resulting environmental load can be avoided according to the invention and, on the other hand, complex steps for limiting the access of a liquid or gaseous etchant outside the second partial areas to be treated can be avoided.

In some embodiments of the invention, the layer thickness of the coating is, at least in the second partial area, between about 20 nm and about 100 nm or between about 30 nm and about 70 nm prior to the action of the plasma. Such a coating does not impair the dimensional accuracy of the coated component but may already be enough to effect improved sliding properties, a hydrophobization and/or a passivation of the surface.

In some embodiments of the invention, the emulsion and/or the solution can contain or consist of at least one silicone oil and one solvent. In some embodiments of the invention, the solvent can be water or contain water. In other embodiments of the invention, the solvent can contain aliphatic hydrocarbons or aromatic compounds, e.g. hexane, heptane, toluene and/or xylene. Finally, the solvent can also contain an alcohol and/or glycerin and/or ether in order to form an emulsion. In any case, the solvent can be evaporated or be driven from the resulting coating either at ordinary ambient conditions or at a higher temperature in the heating cabinet or furnace so as to leave a coating on the first partial area of the component, said coating containing or consisting of silicone.

In some embodiments of the invention, the coating can contain at least carbon and oxygen and hydrogen and silicon. In some embodiments of the invention, the coating can contain or consist of at least polyorganosiloxane. Due to the action of the plasma, the carbon can be at least partially removed from the coating, such that the coating contains or consists of silicon oxide and/or silicon nitride and/or silicon oxynitride after the plasma treatment.

In some embodiments of the invention, the second partial area is hydrophobic prior to the plasma treatment and hydrophilic after the plasma treatment. In other embodiments of the invention, the second partial area is hydrophilic prior to the plasma treatment and hydrophobic after the plasma treatment. A hydrophobic coating for the purposes of the present description is understood to mean a surface which, when in contact with water, produces a contact angle of more than 90°. For the purposes of the present description, a hydrophilic surface is a surface which, when wetted with water, produces a contact angle of less than 90°. As a result of the plasma treatment, the surface energy can thus be modified to such an extent that the adhesive strength or the wettability with a lubricant, an adhesive, a solder or paint is improved or rendered possible in the first place.

In some embodiments of the invention, the plasma (4) can exert its action for about 0.4 to about 5 seconds or for about 0.5 to about 4 seconds or for about 0.5 to about 1.5 seconds or for about 5 to about 60 seconds. It has been found according to the invention that this short treatment period already suffices to convert a hydrophobic silicone coating into a hydrophilic, silicon-containing compound, such that the method proposed according to the invention can also be used economically in the manufacture of mass products.

In some embodiments of the invention, an atmospheric-pressure plasma can be used which is produced by means of a dielectric barrier discharge. This feature has the effect that a complex vacuum technology can be dispensed with and the method can thus be easily integrated into existing production methods. The use of a dielectric barrier discharge here ensures that the electric power coupled into the plasma remains limited and thermal damage to the component and/or the coating can be avoided.

In some of the embodiments of the invention, a vortex flow of the working gas can be used for producing the plasma. As a result, the discharge can be prolonged. In particular the treatment of the inner surfaces of cylindrical hollow bodies even strengthens this effect since the surfaces support the discharge. Due to this, even slim objects, such a pipes or syringes can be treated.

In some embodiments of the invention, the plasma can contain or consist of an inert gas. In some embodiments of the invention, the inert gas can be or contain a noble gas. In some embodiments of the invention, the plasma can contain or consist of argon. An inert gas plasma in particular ensures that the constituents of the coating are not oxidized or reduced or react in another way with the process gas of the plasma such that the coating is not reacted in an undesired way or is removed from the surface by reactive etching.

In some embodiments of the invention, the plasma can be an active gas which can contain or consist of e.g. nitrogen and/or oxygen.

In some embodiments of the invention, the plasma can be produced by an alternating voltage or a pulsed voltage, which has a frequency of between about 10 kHz and about 30 kHz or between about 15 kHz and about 25 kHz.

In some embodiments of the invention, a plasma beam can be used which is produced by an electric field between the surface of the component and at least one counter electrode by ionizing a working gas flow. In other embodiments of the invention, a plasma jet can be used. In this case, the plasma is produced in the interior of the plasma source by electric fields or electromagnetic radiation and driven from the source by the working gas flow. In some embodiments of the invention, the plasma is produced by means of a dielectric barrier discharge. Plasmas produced in such a way produce only minor temperature increases of less than about 50 K or less than about 30 K with respect to the environment, and therefore thermal damage can also be avoided in the case of sensitive surfaces. This is useful e.g. in the treatment of components made of a polymer or other plastic materials.

In some embodiments of the invention, the invention relates to a method for producing a workpiece with at least one first component and at least one second component which are joined together. Here, at least one component is initially coated, as described above, and then at least the second partial area provided for forming the joint is treated with the plasma according to the invention to modify the coating in the partial area as described. In this way, the adhesion of a solder or an adhesive is improved such that the joint has an improved tightness and/or greater adhesive strengths.

In some embodiments of the invention, the joining can be carried out by using an adhesive which is in particular selected from an acrylate and/or polyurethane and/or an epoxy resin and/or a cyanoacrylate. Such adhesives have high adhesive strengths, can easily be processed and have high initial strengths. As a result, the workpiece can be produced rapidly.

In some embodiments of the invention, the invention relates to a workpiece which comprises at least one first component and at least one second component, which are joined together by adhesion, wherein the joint comprises at least one second partial area of a first partial area of the surface of the first component, wherein at least one coating is applied at least on the first partial area of the surface of the first component. At least the second partial area of the coated first partial area was then exposed to a plasma, as a result of which the carbon content of the coating was reduced and/or the bonding conditions of the coating were changed and/or the layer thickness was reduced. The described modifications can increase the adhesive strength of the adhesive bond in such a way that the reliability of the workpiece can be increased. The workpiece can be a finished product or a semi-finished product, which is further processed in subsequent method steps.

In some embodiments of the invention, the carbon content of the coating in the second partial area of the coating (3) can be reduced to less than about 80% or less than about 75% or less than about 70% or less than about 60% of the initial value prior to the plasma treatment.

In some embodiments of the invention, the workpiece can be selected from a pre-filled syringe and/or a packaging and/or a machine component. A machine component can be e.g. a housing which surrounds other components. At least the first and/or the second component of the workpiece can be made from a plastic material, a glass, a metal or an alloy.

The invention shall be explained in more detail below by means of drawings without limiting the general inventive concept.

FIG. 1 shows a component 2 as part of a workpiece. The component 2 is illustrated in FIG. 1 schematically as a plane parallel plate. In other embodiments of the invention, the component 2 can, of course, also adopt more complex forms, e.g. the form of a hollow cylinder or a complex machine element.

The component 2 can be made e.g. from glass, a plastic material, a metal or an alloy. In some embodiments of the invention, the component 2 can be or consist of a composite material which is composed of various materials. The simplified, strictly illustrative presentation of the component 2 in FIG. 1 shall not limit the subject matter of the invention.

Figure 2:
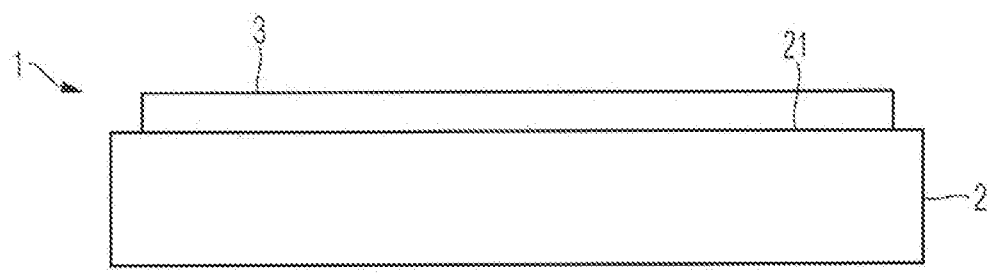
FIG. 2 shows a component with applied coating.

FIG. 2 shows the application of a coating 3 in a first partial area 21 of the component 2. In some embodiments of the invention, the first partial area 21 can comprise the entire surface of the component 2 or the entire area of a cavity or an internal space. In other embodiments of the invention, the first partial area 21 can represent a partial coating of the surface of component 2, such that other partial areas remain uncoated or are coated with another coating material or another coating method.

The coating 3 is produced by applying layer-forming substances which are available as an emulsion or solution in a solvent. For the purposes of the present description, the carrier substance of an emulsion shall also be referred to as a solvent although the layer-forming substances do not chemically dissolve therein but only emulsify or disperse.

Non-polar solvents, e.g. aromatic hydrocarbons, or also water can be used as solvents. In some embodiments of the invention, the layer-forming substances of the coating 3 can be siloxanes or a silicone oil.

Having applied the emulsion and/or the solution by application using a doctor blade, immersion, spraying, painting or printing, the solvent is removed from the coating 3 e.g. by a thermal post-treatment. In addition, the layer-forming substances can cross-link with one another as a result of the post-treatment and form e.g. a poly(organo)siloxane. Moreover, the bonding forces between the coating 3 and the workpiece 2 can be formed as a result of the heat treatment, e.g. in the form of covalent bonds or van der Waals bonds. The application of the coating 3 can be preceded by an optional cleaning step, at least of the first partial area 21. In other embodiments of the invention, the coating 3 can consist of a plurality of individual layers which are applied on top of one another.

Figure 3:
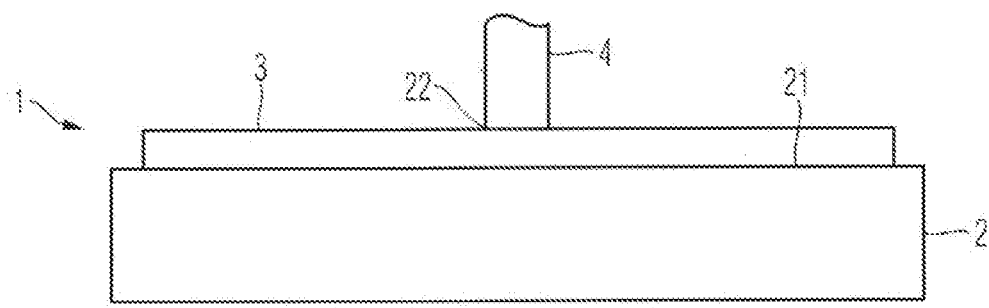
FIG. 3 explains the plasma treatment of a partial area of the component.

FIG. 3 shows a subsequent method step. In this method step, the coating 3 or at least a second partial area 22 of the coating 3 is exposed to a plasma 4. As a result, the layer thickness and/or the bonding conditions and/or the inventory of elements and/or the wetting behavior of the coating 3 are modified in the second partial area 22.

In some embodiments of the invention, the plasma 4 can be an atmospheric pressure plasma, such that the use of complex vacuum technology is avoided. In some embodiments of the invention, the plasma 4 can be produced with a dielectric barrier discharge which can avoid the introduction of large thermal loads into the second partial area 22. In some embodiments of the invention, the plasma 4 can contain or consist of an inert gas, e.g. a noble gas, such as argon, helium or xenon.

In some embodiments of the invention, the exposure time of the plasma 4 can be between about 45 seconds and about 120 seconds. In other embodiments of the invention, the plasma can exert an action for about 0.4 to about 5 seconds or for about 0.5 to about 4 seconds or for about 0.5 to about 1.5 seconds or for about 5 to about 60 seconds. According to the invention, it has been found that this short treatment period already suffices to convert a hydrophobic silicone coating into a hydrophilic, silicon-containing compound, such that the method proposed according to the invention can also be used economically for the manufacture of mass products. An embodiment of a plasma source, by means of which the plasma beam of the plasma 4 can be produced, is explained in more detail below by means of FIG. 5.

Figure 4:
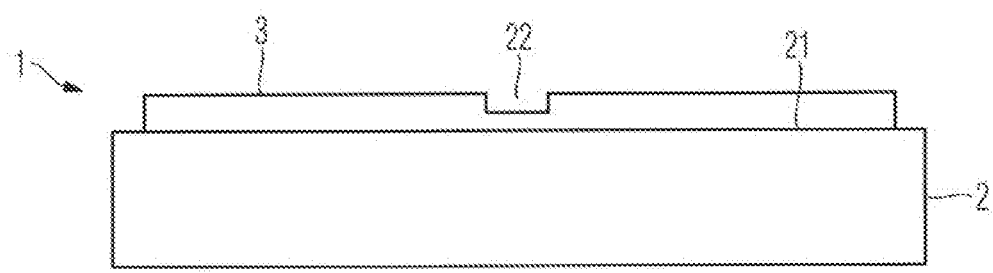
FIG. 4 shows the component after the plasma treatment.

FIG. 4 shows the effects of the plasma treatment in the second partial area 22 of the coating 3 or the partial area 22 of the first partial area 21. As shown in FIG. 4, the plasma treatment reduces the layer thickness by more than about 20% or more than about 25% or more than about 30%. However, it should be noted that the coating 3 is not fully removed but a layer thickness of more than about 70% or more than about 60% or more than about 50% is left in the second partial area 22 after the plasma treatment.

In addition, as a result of the action of the plasma 4, the inventory of elements of the coating 3 can change. For example, the carbon content of the coating 3 can be reduced to less than about 80% or less than about 75% or less than about 70% or less than about 60% of the initial value prior to the plasma treatment.

Finally, in some embodiments of the invention, the wetting behavior of the second partial area 22 can change, i.e. the coating 3 can be originally hydrophobic and become hydrophilic after the action of the plasma 4 in the second partial area 22.

Figure 5:
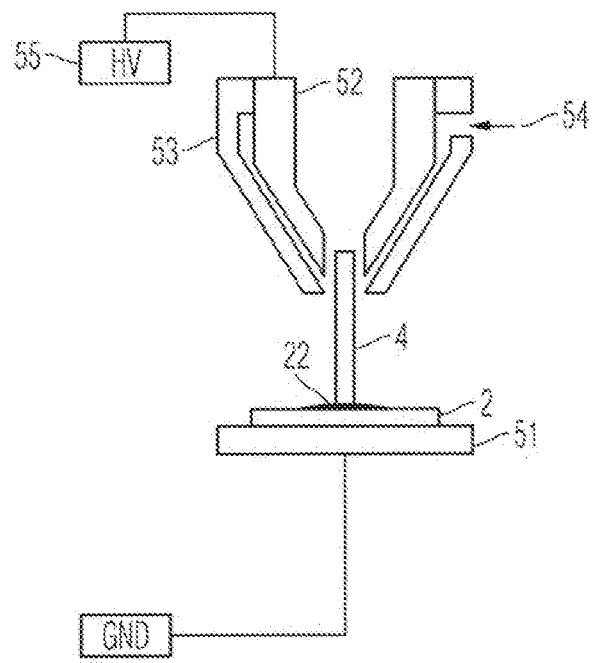
FIG. 5 shows a plasma source which can be used with the proposed method.

FIG. 5 explains in more detail a plasma source which is suitable for carrying out the above described coating method. The plasma source comprises a high voltage electrode 52, which is surrounded by an insulator 53. The high voltage source 52 is designed as a hollow body and can be cylindrical or conical, for example. The insulating body 53 is arranged at a distance from the high voltage electrode 52. A working gas can be introduced in this way into the intermediate space between the high voltage electrode 52 and the insulating body 53 and can be supplied via a gas supply 54. The working gas leaves the high voltage electrode 52 via the opening on the substrate side thereof.

A counter electrode 51 is arranged opposite the opening and can optionally be provided with a dielectric coating. It is thus ensured that in any case a dielectric barrier discharge is ignited between the high voltage electrode 52 and the counter electrode 51. If the substrate itself contains or consists of a dielectric or an insulator, the dielectric coating of the counter electrode 51 can also be omitted.

When the device is operated, a working gas, e.g. argon, is supplied via the gas supply 54. A high-frequency alternating voltage is applied to the high-voltage electrode 52 and is generated by means of a high-voltage source 55. In some embodiments of the invention, the amplitude of the applied high voltage can be between about 2 kV and about 10 kV or between about 5 kV and about 8 kV. The high voltage can be applied as a sinus-shaped alternating voltage or in the form of individual high voltage pulses. The pulse sequence frequency or the alternating voltage frequency can be between about 10 Hz and about 30 kHz. The power converted in the plasma can be determined by means of a measuring capacitor which integrates the transferred charge carriers of a discharge cycle. The thus determined power can be between about 0.5 watt and about 5 watt or between about 1 watt and about 3 watt.

The plasma beam produced in this way has a diameter of about 0.15 mm to about 0.5 mm. When it impinges on the component 2, the bottom widens in such a way that the second partial area 22 can be larger than the diameter of the plasma beam 4. If the second partial area 22 is larger than the beam spot resulting from the geometry of the plasma source, it is possible to process a larger second partial area 22 by sequential treatment with the plasma 4 by shifting the component 2 or the counter electrode 51 with the component 2 arranged thereon. The distance of the beam exit from the surface to be treated can be between about 3 mm and about 8 mm.

Figure 6:
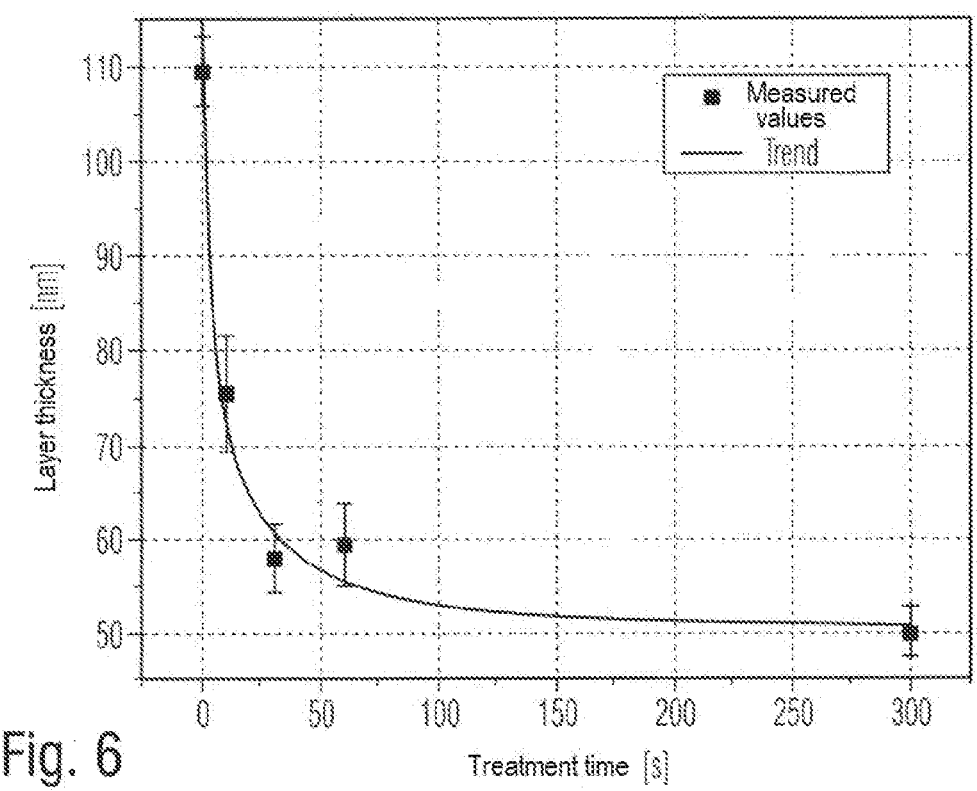
FIG. 6 shows, in an embodiment, the layer thickness decrease over the treatment time.

FIG. 6 explains the ellipsometrically determined layer thickness reduction of the second partial area 22 resulting from the plasma treatment. Here, the treatment period with the plasma beam 4 explained by means of FIG. 5 is plotted on the abscissa and the ellipsometrically determined layer thickness is plotted on the ordinate.

As shown in FIG. 6, the layer thickness prior to the action of the plasma is 110 nm. After an exposure period of about 10 seconds, the layer thickness is already reduced to about 75 nm. After 30 s, the layer thickness is about 57 nm. In the case of a very long treatment period of 300 seconds, the layer thickness drops to about 50 nm. The layer thickness shows an asymptotic pattern in the course of the treatment time. The measured values shown in FIG. 6 suggest that the layer thickness does not drop below 50 nm even if the treatment period is even longer.

FIG. 6 thus shows that no complete removal of the coating is achieved with the plasma treatment according to the invention. Nevertheless, the chemical composition and/or the bonding conditions of the constituents are changed within the coating, as explained in more detail below. This is accompanied by a change in the wetting behavior. The second partial area treated by the plasma is no longer hydrophobic, as originally, but hydrophilic, as a result of which, following the action of the plasma 4, the second partial area 22 is suitable to be joined by means of an adhesive bond or can be coated again with another coating material.

The measured values shown in FIG. 6 were determined by means of a coating 3, which was obtained by means of baked-on siliconization. For this purpose, an emulsion of silicone oil and water is applied and subsequently baked onto the surface of the component 2 by means of heat treatment. The below table shows the inventory of elements of the coating 3 prior to the action of the plasma after 1 second, 10 seconds, 30 seconds, 60 seconds and after 300 seconds. All measured values were obtained by means of photoelectron spectroscopy. Here, monochromatic x-rays are irradiated onto the surface of the coating 3 and the kinetic energy of the photoelectrons is determined. The respective element can be determined from the kinetic energy, and the intensity of the photoelectrons indicates the relative amounts in the coating 3.

| Element | 0 s [atomic %] | 1 s [atomic %] | 10 s [atomic %] | 30 s [atomic %] | 60 s [atomic %] | 300 s [atomic %] |
|---|---|---|---|---|---|---|
| Oxygen (O) | 39.1 | 56.2 | 60.4 | 67 | 66.96 | 66.96 |
| Carbon (C) | 35.8 | 18.93 | 13.9 | 5.6 | 4.14 | 3.63 |
| Silicon (Si) | 25.1 | 24.85 | 25.7 | 27.4 | 28.68 | 29.28 |
| balance | — | — | — | — | 0.27 | 0.13 |

The measurements were obtained after the action of an atmospheric pressure plasma beam with atmospheric air as a working gas, said beam being obtainable e.g. with the device according to FIG. 5. As shown by the above illustrated measured values, the carbon content of the coating rapidly decreases with increasing exposure period to the plasma. This is due to the fact that the methyl groups in the silicone are split off and removed through the gas flow of the working gas of the plasma 4.

Figure 11:
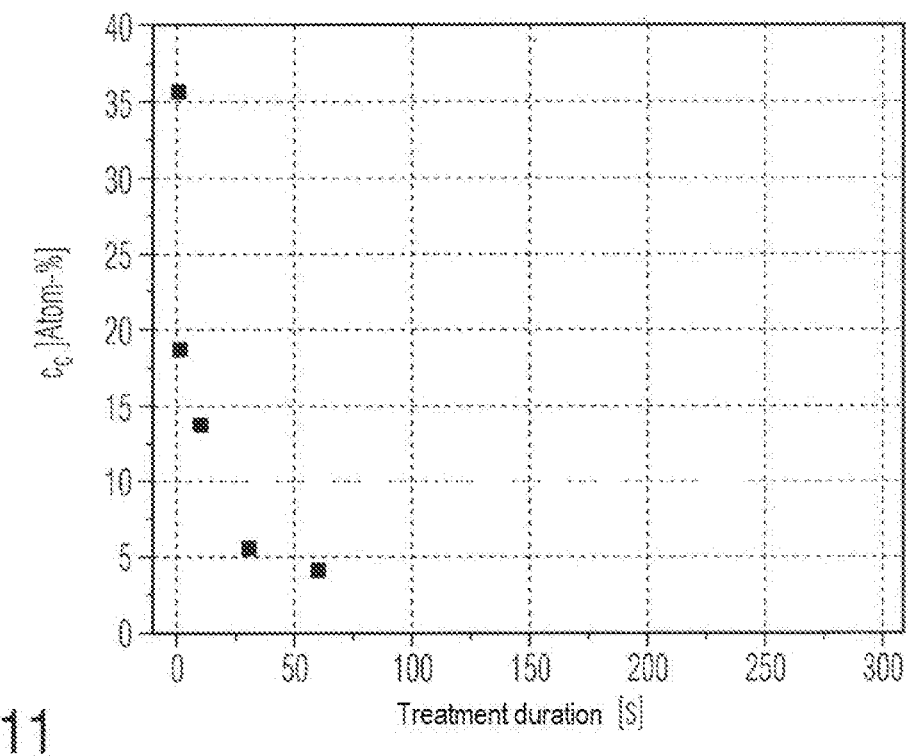
FIG. 11 shows the reduction in the carbon content against the treatment time.

FIG. 11 shows once again graphically the decrease in the carbon content against the treatment duration. The treatment duration is shown on the abscissa and the carbon content is plotted on the ordinate. It is thus illustrated that already very short treatment durations of less than one second up to a few seconds have a significant effect on the coating. Such treatment durations can also be easily achieved in particular in the production of mass-produced articles on the assembly line without considerably delaying the production of the article. It is thus possible to significantly improve the adhesive strength of a subsequent paint and/or adhesion without having to use wet-chemical processes that are dangerous to health.

Figure 7:
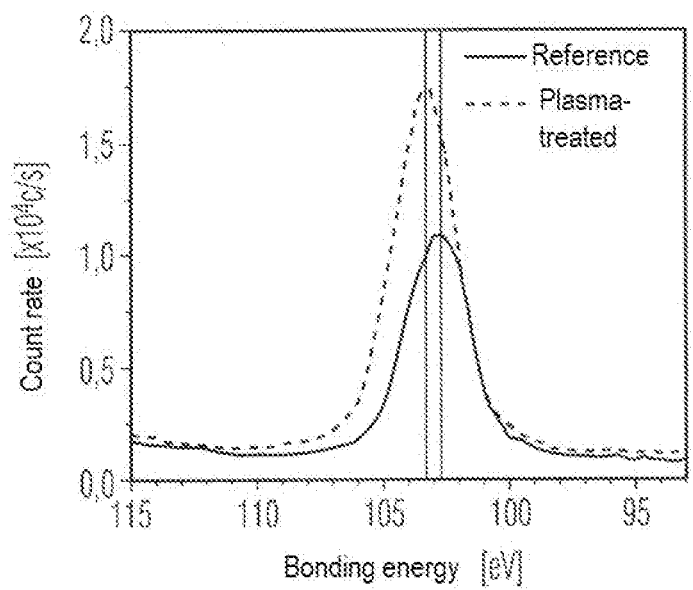
FIG. 7 shows measured results of the photoelectron spectroscopy on a coating according to the invention.

FIG. 7 shows the energetic situation of the silicon $2p$ peak. Here, the bonding energy is plotted on the abscissa and the relative frequency or count rate is plotted on the ordinate. It is clear that the position of the silicon $2p$ level is shifted from 102.6 eV to 103.2 eV by the plasma treatment. The latter value corresponds to the value cited in the literature for silicon dioxide ($SiO_2$). The polymeric silicone layer obviously changes to an amorphous or glass-like layer.

Figure 8:
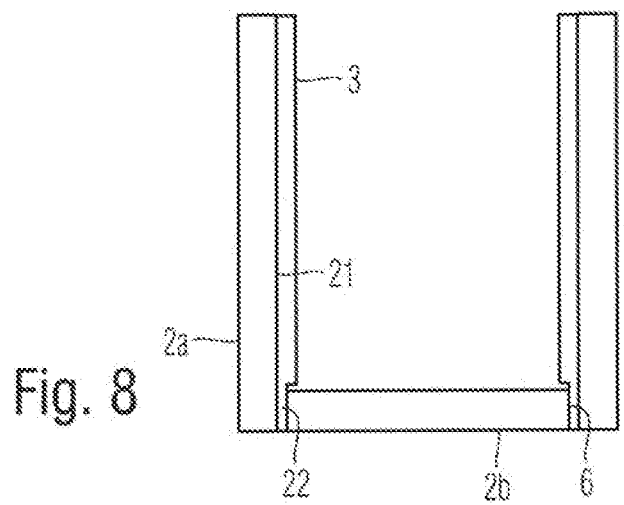
FIG. 8 shows a workpiece according to a first embodiment of the invention.

Possible fields of application of the method according to the invention shall be explained in more detail below. Here, FIG. 8 shows a first example of use of the invention. FIG. 8 shows the cross-section through an approximately cylindrical container having a cylindrical wall 2a, which can be produced e.g. from a pipe portion. The cylindrical wall 2a can be made from a glass or plastic material.

A baked-on siliconization can be applied to the inner side of the cylindrical wall 2a as a coating 3, as described above. For this purpose, a solution and/or an emulsion made of a silicone oil and a solvent is applied and subsequently baked on by treating it in a heating furnace at about 150° C. to about 300° C. The coating 3 has hydrophobic properties, such that the adhesive strength of subsequent adhesive bonds is impaired.

A second component 2b shall be joined to the first component 2a. The second component 2b can be a bottom plate which is formed in complementary fashion to the cylindrical wall 2a and which seals the resulting container downwards in fluid-tight fashion. The bottom plate 2b shall be attached and sealed by means of an adhesive bond 6.

For this purpose, an atmospheric pressure plasma shall act upon a second partial area 22, as described above. On the one hand, this reduces the layer thickness of the coating 3. The chemical composition and the inventory of the elements in the coating 3 are modified at the same time. Having concluded the plasma treatment, the second partial area 22 is hydrophilic. This ensures a good adhesive strength of the adhesive bond 6.

Even though the second component 2b is shown in FIG. 8 without a coating 3, this, of course, does not rule out providing the component 2b with a coating prior to joining, which can also be applied by baked-on siliconization. In this case, the adhesive surface of the component 2b can also be subsequently subjected to a plasma treatment to improve the adhesive strength or to allow an adhesive bond in the first place.

Figure 9:
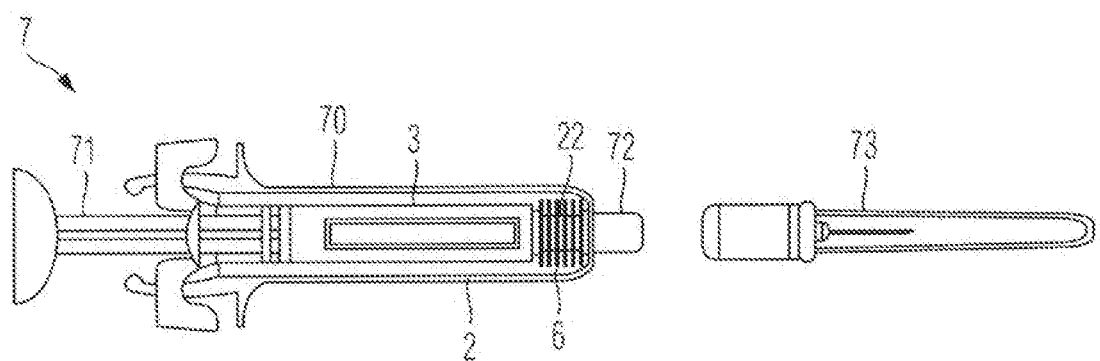
FIG. 9 shows a workpiece according to a second embodiment of the invention.

FIG. 9 shows a pre-filled syringe as a second embodiment of the invention. The pre-filled syringe 7 has an approximately cylindrical syringe body 70. The body 70 represents a first component 2. Pre-filled syringes 7 of the illustrated kind serve as packaging for the medicament contained therein in the manufacturing plant, as a result of which it can be delivered to the physician or patient in a directly read-to-use form.

In order to produce the pre-filled syringe shown in FIG. 9, the syringe body 70 is initially made from a glass tube. For this purpose, the glass tube is cut to size, heated and reshaped in accordance with the desired form.

In the next method step, at least the inner side is sprayed with an emulsion of a solvent and layer-forming substances and then treated in a furnace or heating cabinet. As a result, a large part of the solvent in the emulsion evaporates. At the same time, the silicone contained as a layer-forming substance is covalently bonded to the glass so as to form a layer 3 on the inner side, which contains or consists of polysiloxane. The heat treatment prevents the silicone from undesirably transitioning into the medicament during the subsequent filling, during storage and when the pre-filled syringe 7 is used. At the same time, the siliconization allows an easy sliding of the piston 7, as a result of which the handling of the pre-filled syringe 7 is facilitated.

In the illustrated embodiment, a cone 72 is adhered to the end of the syringe body 70 that is opposite the piston 71, said cone being provided for receiving the injection needle 73. In other embodiments of the invention, the injection needle 73 can also be adhered directly into the syringe body 70 such that the cone 72 can also be omitted.

Since the coating 3 also covers the second partial area 22 provided for receiving the cone 72, the adhesive strength of an adhesive bond 6 is reduced. As a result, the cone 72 can drop out of the syringe body 70 during the transport or during storage and the contents of the pre-filled syringe 7 can leak out.

The invention thus proposes to treat the second partial area 22 with an atmospheric pressure plasma in the above described way. Although the coating 3 is hereby not removed completely, it is inactivated to such an extent that the adhesive bond 6 can be completed reliably. Due to the change in the inventory of elements and/or the bonding conditions of the constituents, the hydrophobic coating 3 in the second partial area 22 can become hydrophilic in order to improve the adhesive strength of the bond 6.

After adhering the cone 72 into the syringe body 70, the pre-filled syringe 7 is prepared to be filled in a manner known per se, i.e. it is cleaned, sterilized and packed. The syringe prepared to be filled in this way is then delivered to the manufacturer of the medicament in order to be filled.

Figure 10:
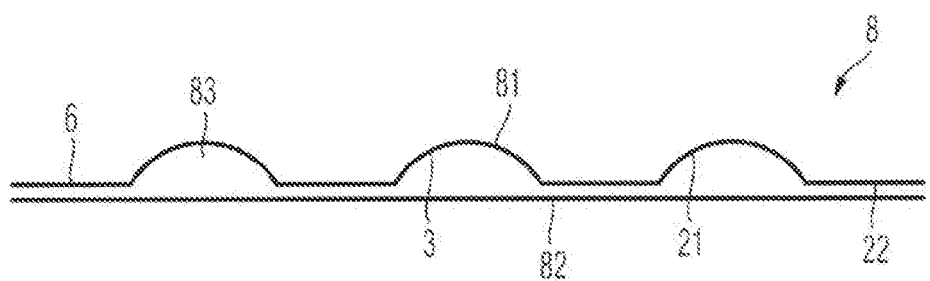
FIG. 10 shows a workpiece according to a third embodiment of the invention.

A third embodiment of the present invention is explained by means of FIG. 10. FIG. 10 shows the cross-section through a blister pack 8. The blister pack contains a first film layer 81, in which cavities 83 are formed. The first film layer 81 can be made of aluminum film or a plastic material. At least the inner side of the cavities 83 is provided with a baked-in siliconization as a coating 3, as explained above. In a subsequent use of the blister pack 8, this prevents the adhering of the packaged product and simultaneously the undesired transition of the silicone oil to the packaged product.

When the first film layer 81 of the blister package is fully siliconized, this prevents a reliable adhesion with a second film layer 82, which is necessary to close the cavities 83 after inserting the packaged product. Therefore, second partial areas 22 between the cavities are treated with the plasma in the described way to inactivate the coating 3 and convert it from a hydrophobic into a hydrophilic state. Then, the cavities 83 can be reliably closed by adhering a second, flat film layer 82 onto the first film layer 81.

Figure 12:
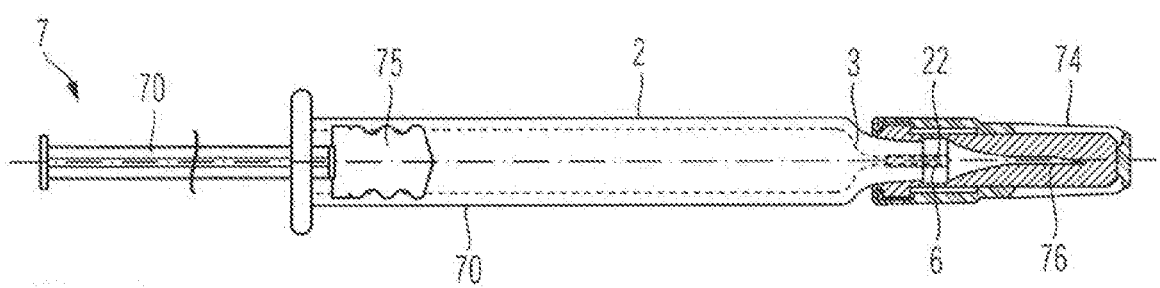
FIG. 12 shows a workpiece according to a fourth embodiment of the invention.

FIG. 12 shows a workpiece according to a fourth embodiment of the invention. The fourth embodiment is also a pre-filled syringe, the principle function of which has already been explained by means of the second embodiment. Equal constituents are designated by the same reference signs, and therefore the below description is limited to the relevant differences.

In order to produce the pre-filled syringe (staked in needle syringe) shown in FIG. 12, the syringe body 70 is initially made of a glass tube. For this purpose, the glass tube is cut to size, heated and molded according to the desired form.

The syringe body 70 can also consist of a plastic material. Plastic syringes are made by known manufacturing methods, e.g. injection molding.

In the next method step, at least the inner side of the syringe body 70 is sprayed with an emulsion made of a solvent of layer-forming substances and subsequently treated in a furnace, e.g. a tunnel kiln or heating cabinet. As a result, a large part of the solvent in the emulsion evaporates. At the same time, the majority of the silicone contained as a layer-forming substance is covalently bonded to the glass so as to form on the inner side a coating 3 which contains or consists of polysiloxane and/or polydimethylsiloxane. The heat treatment serves to prevent the silicone from transitioning in undesired fashion into the medicament in a subsequent filling operation, during storage and when the pre-filled syringe 7 is used. At the same time, the siliconization allows a soft sliding of the plunger 75 so as to facilitate or even allow at all the handling of the pre-filled syringe 7 and/or an application of the medicament.

In the illustrated embodiment, a cannula 76 is adhered at the end of the syringe body 70 that is opposed to the plunger 75.

Since the coating 3 also covers the second partial area 22 provided for receiving the cannula 76, the adhesive strength of an adhesive bond 6 is reduced. It is even possible that the cannula 76 already drops out of the syringe body 70 during the transport or storage and the content of the pre-filled syringe 7 leaks out.

The invention therefore proposes to treat the second partial area 22 in the above described way by means of an atmospheric pressure plasma in such a way that, although the coating 3 is not removed completely, it is inactivated to such an extent that the adhesive bond 6, which can be almost as large as the partial area 22, can be executed reliably. Due to the change in the inventory of elements and/or the bonding conditions of the constituents, the hydrophobic coating 3 can become hydrophilic in the second partial area so as to improve the adhesive strength of the adhesive bond 6.

After gluing the cannula 76 into the syringe body 70, the pre-filled syringe 7 is prepared to be filled in a manner known per se in order, i.e. it is cleaned, sterilized and packaged. Here, the needle protection piece 74 is placed on the cannula 76. This syringe prepared to be filled in this way is then delivered to the manufacturer of the medicament in order to be filled.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

Of course, the invention is not limited to the illustrated embodiments. Therefore, the above description should not be considered to be limiting but explanatory. The below claims should be understood in such a way that a described feature is available in at least one embodiment of the invention. This does not rule out the presence of further features. If the claims and the above description define "first" and "second" embodiments, this designation serves to distinguish between two similar embodiments without determining an order.

The invention claimed is:

1. A method of coating comprising:
applying at least one emulsion and/or one solution at least to a first partial area of a surface of a component, said at least one emulsion and/or said solution containing at least one layer-forming substance;
then heat-treating the component; and
subsequently exposing at least one second partial area of the first partial area to a plasma, wherein a carbon content of the coating in the at least one second partial area exposed to the plasma is reduced to less than 80% of an initial value of the carbon content of the coating prior to exposure to the plasma.

2. The method of claim 1, wherein, at least in the second partial area, the layer thickness of the coating is between 20 nm and 100 nm prior to exposure to the plasma and, due to exposure to the plasma, is reduced in the second partial area by more than 20%.

3. The method of claim 1, wherein the emulsion and/or the solution contains or consists of at least one silicone oil and optionally water, and/or wherein the coating comprises at least carbon and oxygen and hydrogen and silicon, and/or wherein the coating contains at least one poly(organo)siloxane.

4. The method of claim 1, wherein the second partial area is hydrophobic before exposure to the plasma and hydrophilic after exposure to the plasma.

5. The method of claim 1, wherein the plasma contains or consists of an active gas, and wherein the active gas optionally contains or consists of oxygen or synthetic air or atmospheric air.

6. The method of claim 1, wherein the plasma takes effect for 0.4 to 60 seconds, and/or
wherein the plasma includes an atmospheric pressure plasma produced by a dielectric barrier discharge, and/or
wherein the plasma contains or consists of an inert gas and the inert gas optionally contains or consists of a noble gas, and/or
wherein the plasma is formed as a plasma beam or plasma jet which acts at least upon the second partial area.

7. A method for producing a workpiece having at least one first component and at least one second component, the method comprising joining the at least one first component and the at least one second component together, the method further comprising coating the at least one component by the method of claim 1.

8. The method of claim 7, wherein the second partial area of the first partial area comprises at least one joint.

9. The method of claim 7, wherein the joining is by means of an adhesive.

10. The method of claim 9, wherein the adhesive is selected from an acrylate and/or a polyurethane and/or an epoxy resin and/or a cyanoacrylate.

11. A method comprising:
joining at least one first component and at least one second component together at a joint by adhesion, wherein the first component has a surface and a first partial area of the surface, and the joint comprises at least one second partial area of the first partial area;
applying at least one coating to at least the first partial area of the surface of the first component;

exposing at least the second partial area of the first partial area to a plasma after the at least one coating is applied, resulting in one or more of the following:
- a reduction in a carbon content of the at least one coating in the second partial area to less than 80% of an initial value of the carbon content of the at least one coating prior to exposure to the plasma;
- a change of a layer thickness of the at least one coating in the at least one second partial area; or
- a change of bonding conditions and/or wetting behavior of the at least one coating in the second partial area.

12. The method of claim 11, wherein prior to exposure to the plasma, the layer thickness of the at least one coating is between 20 nm and 100 nm at least in the second partial area, and the layer thickness of the at least one coating decreases by more than 20% as a result of exposure to the plasma in the second partial area.

13. The method of claim 12, wherein, in the second partial area, more than 70% of the layer thickness of the at least one coating is left after exposure to the plasma.

14. The method of claim 11, wherein the coating contains at least carbon and oxygen and hydrogen and silicon, and/or wherein the coating contains at least one poly(organo) siloxane.

15. The method of claim 11, wherein the joint comprises an adhesive.

16. The method of claim 15, wherein the joint comprises an acrylate, a polyurethane, an epoxy resin, and/or a cyanoacrylate.

17. The method of claim 11, wherein the workpiece is a pre-filled syringe, a packaging, and/or a machine component.

18. The method of claim 1, wherein, at least in the second partial area, the layer thickness of the coating is between 20 nm and 100 nm prior to exposure to the plasma and, wherein a layer thickness of more than 70% is left in the second partial area after exposure to the plasma.

* * * * *